United States Patent [19]

Friedman

[11] Patent Number: 5,402,783
[45] Date of Patent: Apr. 4, 1995

[54] METHOD OF MINIMIZING DISTORTION TO RADIATION ISODOSE CONTOURS AND OF TARGETING THE DEPTH OF MAXIMUM DOSE AT AN EFFECTIVE TISSUE DEPTH DURING RADIATION THERAPY

[75] Inventor: Robert Friedman, Baton Rouge, La.

[73] Assignee: Eco-Safe International, Inc., Baton Rouge, La.

[21] Appl. No.: 92,557

[22] Filed: Jul. 16, 1993

[51] Int. Cl.6 ............................................. A61B 6/00
[52] U.S. Cl. ............................. 128/653.1; 250/363.01; 250/363.07; 378/65
[58] Field of Search ............... 128/653.1, 653.2, 653.5, 128/660.01, 660.06; 324/309, 318; 601/1, 2, 17; 604/20; 607/153; 378/65; 250/358.1, 362, 363.01, 363.07

[56] References Cited

U.S. PATENT DOCUMENTS

| | | |
|---|---|---|
| 3,839,304 | 10/1974 | Hovey . |
| 4,036,788 | 7/1977 | Steckler . |
| 4,071,508 | 1/1978 | Steckler . |
| 4,331,783 | 5/1982 | Stoy . |
| 4,337,327 | 6/1982 | Stoy . |
| 4,558,093 | 12/1985 | Hatzenbuhler et al. . |
| 4,621,808 | 11/1986 | Orchard et al. . |
| 4,747,819 | 5/1988 | Phipps et al. ............... 604/20 |
| 4,752,285 | 6/1988 | Petelenz et al. ............ 604/20 |
| 4,774,957 | 10/1988 | Nambu et al. ............... 128/653.2 |
| 4,938,233 | 7/1990 | Orrison, Jr. . |
| 5,016,615 | 5/1991 | Driller et al. ................ 604/20 |
| 5,039,774 | 8/1991 | Shikinami et al. .......... 128/653.1 |
| 5,071,602 | 12/1991 | Nambu et al. ............... 128/653.5 |
| 5,087,242 | 2/1992 | Petelenz et al. ............ 604/20 |
| 5,147,291 | 9/1992 | Cukier ........................ 604/20 |
| 5,227,727 | 7/1993 | Segawa et al. ............. 324/318 |

OTHER PUBLICATIONS

Direct Mail Flyer from W & T Medical Systems, Inc., P.O. Box 888, Ambler, Pa. 19002, Telephone #(215) 628-2727 entitled T.E.M. TM The Pliable Bolus (Tissue Equivalent Material), Jun. 18, 1993.

*Primary Examiner*—Krista M. Pfaffle
*Attorney, Agent, or Firm*—William David Kiesel; Robert C. Tucker

[57] ABSTRACT

A method for minimizing the distortion of the isodose contours created by tissue surface irregularities and for targeting the depth of maximum dose at an effective tissue depth during radiation therapy to a treatment field from a source is described. The method comprises the steps of: (i) placing an effective thickness of an anionic polymeric hydrogel into operational contact with the treatment field prior to the therapy; and (ii) administering the therapy in a manner such that the effective thickness of the anionic polymeric hydrogel is between the source and the treatment field, and the anionic polymeric hydrogel is in operational contact with the treatment field while the therapy is being administered. A preferred method is also described for marking the surface area of electron bombardment and radiation treatment portals on individuals prior to diagnostic magnetic resonance imaging. The method comprises the steps of: locating the area on the individual desired to be marked; selecting an appropriate marking device comprising an anionic polymeric hydrogel formed into a shape having at least one dimension of sufficient thickness to be discernable in a magnetic resonance image; placing the marking device at a location sufficiently near the located areas to appear in the magnetic resonance image and to indicate the location of the located area; and performing the magnetic resonance imaging while the marking device remains in place.

6 Claims, No Drawings

METHOD OF MINIMIZING DISTORTION TO RADIATION ISODOSE CONTOURS AND OF TARGETING THE DEPTH OF MAXIMUM DOSE AT AN EFFECTIVE TISSUE DEPTH DURING RADIATION THERAPY

BACKGROUND OF THE INVENTION

This invention relates generally to a method of administering radiation therapy and more particularly to a method of minimizing the distortion of the radiation isodose contours created by tissue surface irregularities and of targeting the depth of maximum dose at an effective tissue depth during radiation therapy to a treatment field from a radiation source.

Magnetic resonance imaging and radiation therapy are well known and effective treatment and diagnostic methods for various types of disease. During the treatment of skin cancers and various other conditions, it is sometimes therapeutically beneficial to expose surface and near-surface tissues of the human body to predetermined doses of radiation. Although beneficial, radiation therapy of surface and near-surface tissues is difficult to perform.

One of the principal difficulties associated with surface and near-surface radiation therapy when using radiation in the mega-electron-volt range is applying the maximum dose applied to the treatment field. The treatment field is that tissue, such as a tumor, for which application of the radiation is the prescribed treatment. Dosage control is difficult because radiation, in the form of an electrons, which strikes a relatively high density structure like human tissue has its highest therapeutic intensity level, not at the surface of the tissue, but at a depth below the surface. The depth at which the highest dose of radiation is received is known as the depth of maximum dose. Depth of maximum dose is a function of the energy imparted to the electrons by the source and the physical properties of the material at which the electrons are targeted.

When the electrons first enter tissue they strike atoms knocking electrons free from some of them. The electrons which have been knocked free are known as secondary electrons. The secondary electrons, in turn, knock other electrons free; creating geometric growth in the number of free electrons within the tissue, until a portion of the energy in the original electrons is attenuated. The tissue depth at which the chain reaction knocks free the largest number of electrons is the depth of maximum dose. This depth, depending on the energy level of the electrons emitted from the source, can range from a few millimeters to a few centimeters.

It is, therefore, the general practice, when administering radiation therapy to treatment fields comprising surface and near-surface tissue structures, to bolus the area above the site to receive the radiation. Bolusing an area means placing a material having radiological characteristics equivalent to tissue in contact with the tissue surface; between the tissue surface and the radiation source. The depth of maximum dose is then raised to the treatment field by selecting and applying an appropriate thickness of bolus material to the area above the treatment field tissue.

Bolusing materials are also used when radiation in the form of photons is used during radiation therapy. There are two purposes for bolusing when using this form of radiation. The first purpose is to adjust the depth of maximum dose to a desired level. The second purpose is to minimize the distortion of the radiation isodose contours due to tissue surface irregularities.

An isodose contour is a representation of dosage level information. Those tissue areas receiving the same radiation dosage level form an isodose contour.

When radiation enters tissue through an area of surface tissue which is normal to the direction of propagation of the wave, the isodose contours form a uniform gradient parallel to the plane of the surface tissue. This type of isodose contour is known as an homogeneous isodose contour.

When radiation enters tissue through an area of surface tissue which is not normal to the direction of propagation of the wave, the direction of propagation changes at the air to surface tissue interface. This change in direction causes interference patterns and creates isodose contours having various shapes. This type of isodose contour is known as a non-homogeneous isodose contour. As can be expected, those surface tissue areas having the greatest surface variations, such as the buttocks area, create greater non-homogeneity in the isodose contours.

It is generally known to use bolus material to increase the homogeneity of the isodose contours during radiation therapy. This is accomplished by using bolus material to increase the quantity of surface area normal to the direction of propagation of the radiation wave by either (i) placing a sheet of bolus material over the irregularly shaped surface tissue or by (ii) placing bolus material within the surface variations themselves. However, because of the great variety of surface variations which exist and the mechanical properties of conventional bolusing materials, air pockets are often formed between the bolusing material and the tissue surface.

The formation of air pockets is hard to avoid when using conventional bolusing materials during radiation therapy to irregularly shaped tissue structures. For instance, when it is necessary to apply radiation to a structure such as the ear, the ear is bolused and the radiation administered. Because of the ears physical form, the bolusing material may not conform entirely to the contours of the surface structure of the ear and air pockets may be formed. These air pockets can create isodose contour distortion; limiting the benefit realized by the use of the bolus. It is, therefore, desirable to have a method of bolusing prior to radiation therapy which will minimize air pocket formation.

The solution to minimizing air pocket formation is to preform the bolus into a shape which conforms to the shape of the surface tissue. This can be accomplished by (i) making a negative latex cast of the tissue structure, (ii) making a positive mold from the negative cast, and (iii) creating a bolus out of a material such as bees wax using the positive mold. This is a time consuming and expensive process. A bees wax bolus for an ear can take as long as eight hours to manufacture. A method of preforming boluses which is quick and inexpensive is therefore desirable.

During the course of radiation treatment, it necessary to perform magnetic resonance imaging of the target field and surrounding tissue structures to evaluate treatment progress and the degree of radiation damage to the surrounding tissue structures caused by the therapy. A treatment portal is the volume of non-treatment field tissue that the radiation must pass through in order to treat the treatment field tissue. The treatment portal begins at one skin surface, continues through the patient and terminates at the opposite skin surface of the patient. Magnetic resonance imaging is helpful in reducing the amount of non-treatment field tissue damage by providing the prescribing physician with information regarding the degree of damage done to non-treatment field tissue. It is important in evaluating and detecting damage to non-treatment field tissue areas that the physician be able to determine from the MRI the treatment portal through which the radiation treatments are directed. It is required during prolonged radiation treatments to change the treatment portal in order to minimize damage to tissue structures within a given treatment portal. A method for marking the entrance and exit portions of the portal on the patient prior to performing the MRI is therefore desirable in order to minimize the damage to non-treatment field tissue areas.

SUMMARY OF THE INVENTION

Therefore, it is an object of the present invention to provide a method of bolusing a tissue area prior to radiation therapy which will allow the radiation therapist to adjust the depth of maximum dose such that the depth of maximum dose coincides with the depth of the treatment field.

It is another object of the present invention to provide a method of bolusing prior to radiation therapy which will allow the radiation therapist to minimize the distortion of the radiation isodose contours caused by surface tissue irregularities.

It is a further object of the present invention to provide a method of marking treatment portals during magnetic resonance imaging in order to minimize damage done to non-treatment field tissue during radiation therapy.

Accordingly, a method for minimizing the distortion of the isodose contours created by tissue surface irregularities and for targeting the depth of maximum dose at an effective tissue depth during radiation therapy to a treatment field from a source is described. The method comprises the steps of: (i) placing an effective thickness of an anionic polymeric hydrogel into operational contact with the treatment field prior to the therapy; and (ii) administering the therapy in a manner such that the effective thickness of the anionic polymeric hydrogel is between the source and the treatment field, and the anionic polymeric hydrogel is in operational contact with the treatment field while the therapy is being administered.

A preferred method is also described for marking the surface tissue areas of a radiation treatment portal on individuals prior to diagnostic magnetic resonance imaging. The method comprises the steps of: (i) locating the area on the individual desired to be marked; (ii) selecting an appropriate marking device comprising an anionic polymeric hydrogel formed into a shape having at least one dimension of sufficient thickness to be discernable in a magnetic resonance image; (iii) placing the marking device at a location sufficiently near the located areas to appear in the magnetic resonance image and to indicate the location of the located area; and (iv) performing the magnetic resonance imaging while the marking device remains in place.

PREFERRED EMBODIMENTS OF THE INVENTION

The method of the present invention comprises the step of placing an effective thickness of a material having a water content, substantially the same, by volume, as tissue, into operational contact with a portion of the treatment portal consisting of surface tissue at a location which, during the treatment, will be between the tissue of the treatment field and the radiation source. The suitable materials for use in this method consist of anionic polymeric hydrogels comprising polyacrylamide monomer acrylamide hooked together cross-linked (serpentine) with bis-acrylamide anti-oxidant persulfate catalyzed with TEMED. Substantially the same as tissue means the percentage of water content by volume of anionic polymeric hydrogel is preferably between 40 and 90%, more preferably between 60 and 90% and most preferably between 75 and 90%. An effective thickness means a thickness sufficient to move the location of the depth of maximum dosage within the individual receiving the radiation therapy. Operational contact means having no substantial quantity of material with the radiological properties of air between the anionic hydrogel and the portion of the treatment portal consisting of surface tissue. The foregoing description of the type of anionic polymeric hydrogel to be used in the method, as well as, the description of an "effective thickness" and "operational contact" apply to all the preferred embodiments of the method of the invention to be described below.

In a preferred method, an anionic polymeric hydrogel mix, whose exothermic reaction when mixed with water is less than the amount required to thermally burn tissue, is selected as the bolusing material. A sufficient quantity of the mix to allow application of an effective thickness over the area to be treated is then mixed with a quantity of water sufficient to form a fluid mixture which has the desired percentage of water content and will gel. The mixture is next allowed to sit until the mixture is partially gelled. Partially gelled means sufficiently gelled to form a mound when poured onto a flat surface but still sufficiently fluid to flow into and fill open cavities within the surface upon which it is poured. Once the mixture is partially gelled, the partially gelled mixture is poured over the area of tissue to be bolused. In a more preferred method the partially gelled mixture is allowed to completely gel before treatment is administered. Completely gel means no longer capable without outside intervention of flowing into and filling open cavities within the surface in which it is in contact.

A preferred anionic hydrogel mix for use in this preferred method is a hydrogel mix available under the trade name, RAD-X, from either JRM Chemical Incorporated, Cleveland, Ohio; or ZAXIS, Inc., Cuyahoga Falls, Ohio.

In a still more preferred method the partially gelled mixture is shaped after being applied to the area of the body to be bolused and before the partially gelled mixture completely gels. The shaping may be accomplished by any method which achieves the desired shape. Methods such as hand shaping or casting the bolus by placing a mold or containment structure, constructed of a material which will not adhere to the completely gelled mixture, around the area to be bolused may be used. A preferred method of shaping the partially gelled mixture is smoothing the surface of the partially gelled mixture with a flat edged shaping tool such as a spatula. The spatula is manipulated such that a planar surface is formed wherein the planar surface may be positioned within a plane normal to the direction of propagation of the radiation wave emitted from the source.

Since the mixture is applied in a partially gelled state, the partially gelled mixture flows into and fills the contours and open cavities in the surface to which it is applied. The resulting bolus, therefore, has a minimal amount of air pocket formation. Also, because the anionic polymeric hydrogel selected has a water content substantially the same as tissue, the resulting bolus closely approximates the radiological characteristics of tissue. Thereby raising the depth of maximum dose within the individual receiving the radiation therapy by about the same quantity as the thickness of anionic polymeric hydrogel applied. The planar surface formed in a preferred embodiment also provides a uniform surface normal to the direction of propagation minimizing the distortion of the isodose contours due to surface tissue irregularities.

Another method of the invention, for use over tissue areas with a non-irregular topography, requires the use of an anionic polymeric hydrogel in the form of a sheet as the bolusing material. Examples of areas exhibiting a non-irregular topography are a person's back and a person's thigh. Once the depth of the treatment field and the depth of maximum dose is determined, the required thickness of anionic polymeric hydrogel sheeting is selected. For instance, when the depth of maximum dose is determined to be 1.5 centimeters and the treatment field is cancerous tissue 0.5 centimeters below the surface, the appropriate thickness of anionic polymeric hydrogel sheeting would be about 1 centimeter. Once the desired thickness is selected, the hydrogel sheet is placed into operational contact with the treatment field. The technician then manually positions the hydrogel sheet in a manner to eliminate air pockets between the hydrogel sheet and the treatment field. A preferred method of positioning the sheet to eliminate air pockets is to run a hand over the sheet, in a squeegee like motion, from one edge of the sheet to the other. A preferred anionic polymeric hydrogel sheet for use is a sheet of RAD-X between 0.5 and 2 centimeters thick which is available from either of the above named companies.

A further preferred method of the invention is useful when shielding devices are used in the radiation therapy of an area such as the face. It is a standard procedure, when administering radiation therapy to such an area, to place a shielding device over the general area. The shielding device has an aperture forming a passageway entirely through the shielding device. The aperture is positioned over the treatment field and treatment is performed through the aperture. The shield is generally constructed of a radio opaque material such as lead or cerrobend. The purpose of the shielding device is to protect radiation sensitive tissues such as the cornea by blocking the radiation.

In this embodiment of the method a hydrogel mix of the above described type is mixed and allowed to partially gel. Once the mixture has partially gelled, the aperture is filled to at least an effective thickness in a manner such that a portion of the partially gelled mixture would be in operational contact with the area of tissue forming the treatment portal when the shield is in place during the therapy and such that the aperture no longer forms a passageway through the shielding device. The partially gelled mixture is then allowed to completely gel.

In a preferred method, the hydrogel mix selected for use has an exothermic reaction when mixed with water less than the amount required to thermally burn tissue. This preferred method requires the additional steps of (i) positioning the shielding device in place prior to filling the aperture to at least an effective thickness with the partially gelled mixture, and (ii) allowing the shielding device to remain in place until the partially gelled mixture has completely gelled. A preferred anionic polymeric hydrogel mix for use with this preferred method is also RAD-X.

In another method of the invention, for use during magnetic resonance imaging (MRI), the anionic polymeric hydrogel is formed into shapes. At least one dimension of the shape must be of sufficient thickness to be discernable in a magnetic resonance image; the other dimensions must be sufficient to allow arrangement of the shapes into geometric configurations such as circles, numerals, letters, arrows, etc.. A thickness of hydrogel which is sufficient to be discernable in a magnetic resonance image is a thickness of at least 1 millimeter. The method comprises the steps of (i) placing the shapes into a configuration indicating the surface location of treatment portals used during radiation therapy and in a location which will appear in the MRI, prior to performing the MRI, and (ii) allowing the shapes to remain in place during the magnetic resonance imaging procedure. A preferred method uses strip shaped shapes of a thickness and width between 0.3 and 0.7 centimeters and of any desired length. Another preferred method uses precut geometric shapes cut from a sheet of an anionic polymeric hydrogel between 0.3 and 0.5 centimeters thick.

Since the anionic polymeric hydrogel has a high anion content, it has a distinct appearance in magnetic resonance images. This distinct appearance allows the prescribing physician to more easily locate the tissue within the treatment portal. This helps the physician determine the degree of damage to non-treatment field tissues and to select alternative treatment portals for future therapeutic treatments.

There are of course alternate embodiments which have not been specifically mentioned, but which are obvious and are intended to be included within the scope of the invention as defined by the following claims.

What I claim is:

1. A method for minimizing distortion of isodose contours created by tissue surface irregularities and for targeting the depth of maximum dose at an effective tissue depth during radiation therapy to a treatment field from a source, said method comprising the steps of:
    placing an effective thickness of an anionic polymeric hydrogel into operational contact with said treatment field prior to said therapy; and
    administering said therapy in a manner such that said effective thickness of said anionic polymeric hydrogel is between said source and said treatment field, and said anionic polymeric hydrogel is in operational contact with said treatment field while said therapy is being administered.

2. A method for maximizing homogeneity of a photon beam and for targeting the depth of maximum dose at an effective tissue depth during radiation therapy to a treatment field from a source, said method comprising the steps of:
    measuring a sufficient quantity of an anionic polymeric hydrogel mix having at least two constituent parts and which is mixable with water to allow application of an effective thickness to the desired said treatment field;

mixing said quantity of anionic polymeric hydrogel mix with a sufficient quantity of water to form a mixture which will gel;

allowing said mixture to stand a sufficient amount of time to become a partially gelled mixture;

pouring an effective thickness of said partially gelled mixture into operational contact with at least said treatment field; and administering said therapy in a manner such that said effective thickness of said partially gelled mixture is between said source and said field, and said partially gelled mixture is in operational contact with at least said treatment field while said therapy is being administered.

3. A method according to claim 2 wherein said method further comprises the step of allowing said partially gelled mixture to completely gel prior to administering said therapy.

4. A method according to claim 2 wherein said method further comprises the step of shaping said partially gelled mixture after said partially gelled mixture is poured into operational contact with said treatment field and prior to administering said therapy.

5. A method according to claim 4 wherein said step of shaping comprises shaping the partially gelled mixture into a shape having a surface which may be positioned in a plane substantially parallel to said wave-front emitted from said source during said therapy.

6. A method according to claim 5 wherein said method comprises the further step of positioning said surface within a plane substantially parallel to said wave-front to be emitted from said source prior to said radiation therapy.

* * * * *